(12) United States Patent
Xu et al.

(10) Patent No.: US 8,981,170 B2
(45) Date of Patent: Mar. 17, 2015

(54) PROCESS FOR PRODUCING CYCLOALKYLAROMATIC COMPOUNDS

(75) Inventors: Teng Xu, Houston, TX (US); Wenyih F. Lai, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 52 days.

(21) Appl. No.: 13/703,239

(22) PCT Filed: Jun. 28, 2011

(86) PCT No.: PCT/US2011/042161
§ 371 (c)(1),
(2), (4) Date: Jan. 21, 2013

(87) PCT Pub. No.: WO2012/024026
PCT Pub. Date: Feb. 23, 2012

(65) Prior Publication Data
US 2013/0172514 A1     Jul. 4, 2013

Related U.S. Application Data

(60) Provisional application No. 61/375,351, filed on Aug. 20, 2010.

(30) Foreign Application Priority Data

Sep. 27, 2010  (EP) .................................. 10179990

(51) Int. Cl.
| | |
|---|---|
| C07C 2/66 | (2006.01) |
| C07C 2/74 | (2006.01) |
| C07C 4/06 | (2006.01) |
| C07C 6/12 | (2006.01) |
| C07C 37/08 | (2006.01) |
| C07C 45/53 | (2006.01) |
| C07C 407/00 | (2006.01) |

(52) U.S. Cl.
CPC ... *C07C 2/74* (2013.01); *C07C 4/06* (2013.01); *C07C 6/126* (2013.01); *C07C 37/08* (2013.01); *C07C 45/53* (2013.01); *C07C 407/00* (2013.01); *C07C 2101/14* (2013.01); *C07C 2521/06* (2013.01); *C07C 2521/12* (2013.01); *C07C 2521/16* (2013.01); *C07C 2523/30* (2013.01); *C07C 2529/08* (2013.01); *C07C 2529/70* (2013.01); *C07C 2529/74* (2013.01); *C07C 2529/76* (2013.01); *C07C 2529/80* (2013.01); *C07C 2529/83* (2013.01); *C07C 2529/85* (2013.01)
USPC .......................................... 585/467; 585/455

(58) Field of Classification Search
CPC .......... C07C 2/74; C07C 13/28; C07C 37/08; C07C 45/53
USPC .................................... 585/467, 455
See application file for complete search history.

(56) References Cited

U.S. PATENT DOCUMENTS

| | | | |
|---|---|---|---|
| 3,786,106 A | 1/1974 | Zuech et al. | |
| 3,829,516 A | 8/1974 | Zuech et al. | |
| 3,864,421 A * | 2/1975 | Suggitt | ........................ 585/263 |
| 3,962,362 A | 6/1976 | Suggitt | |
| 4,870,217 A | 9/1989 | Knifton | |
| 5,098,684 A | 3/1992 | Kresge et al. | |
| 5,198,203 A | 3/1993 | Kresge et al. | |
| 5,304,363 A | 4/1994 | Beck et al. | |
| 5,869,417 A * | 2/1999 | Woo et al. | ..................... 502/107 |
| 6,037,513 A | 3/2000 | Chang et al. | |
| 6,049,018 A | 4/2000 | Calabro et al. | |
| 6,720,462 B2 | 4/2004 | Kuhnle et al. | |
| 7,579,511 B1 | 8/2009 | Dakka et al. | |
| 2013/0274089 A1 * | 10/2013 | Schwarzer et al. | ............. 502/74 |

* cited by examiner

*Primary Examiner* — Thuan D Dang
(74) *Attorney, Agent, or Firm* — Jamie L. Sullivan; Siwen Chen

(57) ABSTRACT

In a process for producing a cycloalkylaromatic compound, an aromatic compound, hydrogen and at least one diluent are supplied to a hydroalkylation reaction zone, such that the weight ratio of the diluent to the aromatic compound supplied to the hydroalkylation reaction zone is at least 1:100. The aromatic compound, hydrogen and the at least one diluent are then contacted under hydroalkylation conditions with a hydroalkylation catalyst in the hydroalkylation reaction zone to produce an effluent comprising a cycloalkylaromatic compound.

22 Claims, No Drawings

PROCESS FOR PRODUCING CYCLOALKYLAROMATIC COMPOUNDS

PRIORITY CLAIM

This application is a National Stage Application of International Application No. PCT/US2011/042161 filed Jun. 28, 2011, which claims priority to U.S. Provisional Application Ser. No. 61/375,351 filed Aug. 20, 2010 and European Application No. 10179990.6 filed Sep. 27, 2010, the disclosures of which are fully incorporated herein by their reference.

FIELD

The present invention relates to a process for producing cycloalkylaromatic compounds and, in particular, cyclohexylbenzene.

BACKGROUND

The production of cycloalkylaromatic compounds, such as cyclohexylbenzene, is a commercially important reaction since the latter has potential as a source of phenol and cyclohexanone, which are important products in the chemical industry with utility in, for example, the production of phenolic resins, bisphenol A, $\epsilon$-caprolactam, adipic acid, and plasticizers.

Currently, the most common route for the production of phenol is the Hock process via cumene. This is a three-step process involving alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the demand for propylene is likely to increase. Thus, a process that does not require propylene as a feed and coproduces higher ketones, rather than acetone, may be an attractive alternative route to the production of phenol.

One such process involves the catalytic hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513, in which the hydroalkylation catalyst is a bifunctional catalyst comprising at least one hydrogenation metal component and a molecular sieve of the MCM-22 family.

However, one problem of producing phenol via benzene hydroalkylation is that the hydroalkylation process inevitably produces significant quantities of by-products in addition to the desired cyclohexylbenzene. Among the more significant of these by-products are cyclohexane, dicyclohexylbenzene, dicyclohexane and methylcyclopentylbenzenes. Although many of these impurities can be removed by down-stream processing steps, such steps necessarily add cost to the overall process and hence there is significant interest in improving the cyclohexylbenzene selectivity of the hydroalkylation process.

Following extensive study of the hydroalkylation reaction, it is now believed that one mechanism for the production of unwanted by-products is the slow mass transport of reagents and products since the process is normally conducted in the liquid phase at low temperature. Another potential source of by-product formation is believed to be reactive intermediates, such as cyclohexene, since the latter can readily isomerize to produce methylcyclopentene and dimerize in the presence of hydrogen to produce dicyclohexane.

According to the present invention, it has now been found that the amount of by-products generated in the hydroalkylation reaction can be reduced by the addition of a diluent to the reaction. Although the reason for this result is not fully understood, it is believed that the diluent improves mass transport by facilitating movement of the cyclohexylbenzene away from the active sites of the catalyst and hence minimizing subsequent reactions such as dialkylation. In addition, the use of a diluent will reduce the steady state concentration of reactive intermediates, such as cyclohexene, thereby reducing side reactions involving these intermediates, such as isomerization and dimerization. Finally, the addition of a diluent is believed to assist in removal of heat of reaction, thereby ensuring more homogeneous heat distribution and hence improving cyclohexylbenzene selectivity.

U.S. Pat. No. 3,786,106 discloses a process for reacting an aromatic compound, such as benzene, with a cycloolefin, such as cyclohexene, to produce a cycloalkylaromatic compound, such as cyclohexylbenzene, over an active clay catalyst. In addition, the '106 patent refers to adding a diluent to the process in the form a straight or branched chain paraffinic hydrocarbon having 5 to 10 carbon atoms. However, the function and amount of the diluent is not disclosed or explained, and the basic process is alkylation rather than hydroalkylation in the presence of hydrogen.

SUMMARY

In one aspect, the invention resides in a process for producing a cycloalkylaromatic compound, the process comprising:

(a) supplying an aromatic compound, hydrogen and at least one diluent to a hydroalkylation reaction zone, wherein the weight ratio of the diluent to the aromatic compound supplied to the hydroalkylation reaction zone as measured at the input to the hydroalkylation reaction zone is in the range of from 1:100 to 100:1 and wherein the molar ratio of hydrogen to the aromatic compound supplied to the hydroalkylation reaction zone as measured at the input to the hydroalkylation reaction zone is in the range from 1:100 to 100:1; and (b) contacting the aromatic compound, hydrogen and the at least one diluent under hydroalkylation conditions with a hydroalkylation catalyst in the hydroalkylation reaction zone to produce an effluent comprising a cycloalkylaromatic compound.

Conveniently, the weight ratio of the diluent to the aromatic compound is in the range of from 1:10 to 100:1.

Conveniently, the weight ratio of the diluent to the aromatic compound is in the range of from 1:10 to 10:1.

Conveniently, the hydroalkylation catalyst comprises at least one hydrogenation metal component, typically selected from Groups 8 to 10 of the Periodic Table of the Elements, such as from palladium, ruthenium, nickel, zinc, tin, and cobalt. Generally, the hydroalkylation catalyst also comprises at least one molecular sieve, particularly an MCM-22 family molecular sieve.

Conveniently, the diluent is at least one compound selected from a straight chain paraffinic hydrocarbon, a branched chain paraffinic hydrocarbon, and a cyclic paraffinic hydrocarbon.

In one embodiment, the aromatic compound is benzene and the cycloalkylaromatic compound is cyclohexylbenzene and wherein the effluent further comprises cyclohexane.

Conveniently, the process further comprises recycling at least a portion of the cyclohexane to the contacting step (a) wherein the cyclohexane is utilized as the at least one diluent.

Conveniently, the process further comprises:

(c) separating at least a portion of the effluent into at least a cyclohexylbenzene-rich stream and a $C_6$ product stream comprising cyclohexane and benzene; and (d) recycling at least a portion of the $C_6$ product stream to the contacting step (a) wherein the cyclohexane in the $C_6$ product stream portion is utilized as the at least one diluent.

In one embodiment, the process further comprises:

(e) supplying a further portion of the $C_6$ product stream to a dehydrogenation dehydrogenation reaction zone;

(f) contacting the further portion of the $C_6$ product stream with a dehydrogenation catalyst in the dehydrogenation reaction zone under dehydrogenation conditions to convert at least part of the cyclohexane in the further $C_6$ product stream portion into benzene; and (g) recycling the benzene from the contacting step (f) to the contacting step (a).

Conveniently, the process further comprises:

(h) oxidizing at least part of the cyclohexylbenzene-rich stream to produce cyclohexylbenzene hydroperoxide; and (i) converting at least part of the cyclohexylbenzene hydroperoxide from the oxidizing step (h) to produce phenol and cyclohexanone.

DETAILED DESCRIPTION

Described herein is a process for producing a cycloalkylaromatic compound by contacting an aromatic compound and hydrogen in the presence of a hydroalkylation catalyst, in which the coproduction of by-products, particularly polyalkylated species, is reduced by adding a diluent to the reaction mixture. The present process is particularly intended for producing cyclohexylbenzene for use as a precursor in the production of phenol and cyclohexanone from benzene. The remaining discussion will therefore focus on this particular embodiment, although it is to be appreciated that the present process is equally applicable to the production of other cycloalkylaromatic compounds.

Production of the Cyclohexylbenzene

In the present process, cyclohexylbenzene is produced by contacting benzene with hydrogen under hydroalkylation conditions in the presence of a hydroalkylation catalyst whereby the benzene undergoes the following reaction (1) to produce cyclohexylbenzene (CHB):

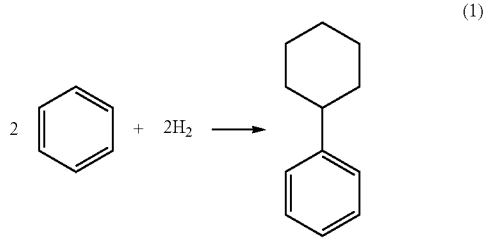 [SMILES: c1ccccc1 ; c1ccc(C2CCCCC2)cc1]

(1)

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values such as a molar ratio of hydrogen to benzene as measured at the input to the hydroalkylation reaction zone in the range from about 0.1:100 to about 100:0.1, for example about 1:100 to 100:1, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, in the present process a diluent, which is substantially inert under hydroalkylation conditions, is supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction such that cyclohexane may be recycled back to the hydroalkylation reaction zone and utilized as the at least one diluent. In one embodiment, the diluent may be supplied to the hydroalkylation reactor in combination with the make-up or recycle benzene. In another embodiment, the diluent supplied to the hydroalkylation reaction zone is derived from a source separate and apart from the benzene fed to the hydroalkylation reaction zone.

The addition of at least one diluent in the quantities identified herein reduces the amount of dicyclohexylbenzene and heavies produced in the hydroalkylation reaction zone as compared to the amount of dicyclohexylbenzene and heavies produced in a hydroalkylation process under the same hydroalkylation conditions wherein substantially no diluent is added to the hydroalkylation reaction zone.

The addition of at least one diluent in the quantities identified herein has been shown to reduce the weight ratio of dicyclohexylbenzene to cyclohexylbenzene in the effluent. Specifically, the addition of the diluent reduces the weight ratio of dicyclohexylbenzene to cyclohexylbenzene contained in the effluent as compared to the weight ratio of dicyclohexylbenzene to cyclohexylbenzene in a hydroalkylation process under the same hydroalkylation conditions wherein substantially no diluent is added to the hydroalkylation reaction zone.

In one embodiment, the addition of the diluent reduces the weight ratio of dicyclohexylbenzene to cyclohexylbenzene contained in the effluent by ten percent as compared to the weight ratio of dicyclohexylbenzene to cyclohexylbenzene in a hydroalkylation process under the same hydroalkylation conditions wherein substantially no diluent is added to the hydroalkylation reaction zone. In other embodiments the reduction in weight ratio of dicyclohexylbenzene to cyclohexylbenzene is 15%, 20%, 25%, 30%, 35%, 40%, 45%, and 50%.

The addition of at least one diluent in the quantities identified herein also has been shown to reduce the weight ratio of heavies to cyclohexylbenzene in the effluent. Specifically, the addition of the diluent reduces the weight ratio of heavies to cyclohexylbenzene contained in the effluent as compared to the weight ratio of dicyclohexylbenzene to cyclohexylbenzene in a hydroalkylation process under the same hydroalkylation conditions wherein substantially no diluent is added to the hydroalkylation reaction zone. "Heavies" is herein defined as any compound having a boiling point greater than that of dicyclohexylbenzene.

In one embodiment, the addition of the diluent reduces the weight ratio of heavies to cyclohexylbenzene contained in the effluent by ten percent as compared to the weight ratio of heavies to cyclohexylbenzene in a hydroalkylation process under the same hydroalkylation conditions wherein substantially no diluent is added to the hydroalkylation reaction zone. In other embodiments the reduction in weight ratio of heavies to cyclohexylbenzene is 15%, 20%, 25%, 30%, 35%, 40%, 45%, and 50%.

Although the amount of diluent is not narrowly defined, generally the diluent is added in an amount such that the weight ratio of the diluent to the aromatic compound as measured at the input to the hydroalkylation reaction zone is in the range of from 1:100 to 100:1; for example in the range of from 1:10 to 100:1, in the range of from 1:100 to 10:1, in the range of from 1:100 to 4:1, and in the range of from 1:10 to 4:1.

Typically, the at least one diluent is added in an amount such that the weight ratio of the diluent to the aromatic compound is at least 1:1000, such as at least 1:200, at least 1:100, at least 1:50, at least 1:25, at least 1:10, at least 1:5. In one embodiment, the weight ratio of the diluent to the aromatic compound is no greater than 1:1 and no greater than 4:1. In another embodiment, the at least one diluent is added such that the weight ratio of the diluent to the aromatic compound supplied to the first dehydrogenation reaction zone is in the range of from 1:1000 to 1000:1, 1:200 to 200:1; from 1:100 to 100:1; 1:75 to 75:1; 1:50 to 50:1; from 1:10 to 10:1, from 1:5 to 5:1, from 1:4 to 4:1, from 1:1 to 100:1, from 1:1 to 10:1, from 3:2 to 100:1, from 3:2 to 10:1, from 2:1 to 100:1, from 2:1 to 10:1, from 3:1 to 100:1, and from 3:1 to 10:1.

In other embodiments, the weight ratio of the diluent to the aromatic compound lower limit may be 1:1000, 1:200, 1:100, 1:10, 1:5, 1:4, 1:3, 1:2, 1:1, 3:2, 2:1, 3:1, and 4:1 and the upper limit weight ratio of the diluent to the aromatic compound may be 2:1, 3:1, 4:1, 5:1, 10:1, 50:1, 100:1, 200:1, and 1000:1 with ranges from any lower limit to any upper limit being contemplated.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa.

In one embodiment, the conditions employed in the present process include a temperature of about 140° C. to about 175° C., particularly about 150° C. to about 160° C., a pressure of about 931 kPag to 1207 kPag (135 psig to about 175 psig), particularly about 1000 kPag to 1069 kPag (145 psig to about 155 psig), a hydrogen to benzene molar ratio of about 0.30 to about 0.65, particularly about 0.45 to about 0.64, and a weight hourly space velocity of benzene of about 0.26 to about 1.05 $hr^{-1}$, particularly about 0.3 to about 0.6 $hr^{-1}$.

The catalyst employed in the hydroalkylation reaction is a bifunctional catalyst comprising a molecular sieve of the MCM-22 family and a hydrogenation metal component. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal component can be employed in the hydroalkylation catalyst, although suitable metal components include palladium, ruthenium, nickel, zinc, tin, and cobalt, with palladium being particularly advantageous. Generally, the amount of hydrogenation metal component present in the catalyst is between about 0.05 and about 10 wt %, such as between about 0.1 and about 5 wt % of the catalyst. In one embodiment, where the MCM-22 family molecular sieve is an aluminosilicate, the amount of hydrogenation metal component present is such that the molar ratio of the aluminum in the molecular sieve to the hydrogenation metal component is from about 1.5 to about 1500, for example from about 75 to about 750, such as from about 100 to about 300. The hydrogenation metal component may be directly supported on the MCM-22 family molecular sieve by, for example, impregnation or ion exchange. The term "metal component" is used herein to include elemental metal or a metal compound or both. To illustrate, the metal component may be purely elemental metal, but could also be at least partly or entirely in another form, such as an oxide, hydride or sulfide form. The weight % (wt %) of the metal component is herein defined as being measured as the metal present based on the total weight of the catalyst composition irrespective of the form in which the metal component is present.

In another embodiment, at least one additional hydroalkylation catalyst component may be added or composited with the hydroalkylation catalyst and may serve as a binder or support or both. One additional hydroalkylation catalyst component may include an inorganic, crystalline, mesoporous material. In this respect, the term "mesoporous" is used herein to refer to porous material having a maximum perpendicular cross-section pore dimension of at least about 13 Angstroms, and generally within the range of from about 13 Angstroms to about 200 Angstroms. In one embodiment, the mesoporous material can be in the range of 20 to 60 Angstroms. In another embodiment, the mesoporous material can be in the range of 20 to 50 angstroms, 20 to 40 angstroms, 20 to 30 angstroms, 30 to 60 angstroms, 30 to 50 angstroms, 30 to 40 angstroms, and 25 to 55 angstroms.

The mesoporous material may layered or non-layered wherein non-layered is herein defined as non-lamellar. In layered (i.e., lamellar) materials, the interatomic bonding in two directions of the crystalline lattice is substantially different from that in the third direction, resulting in a structure that contains cohesive units resembling sheets. Usually, the bonding between the atoms within these sheets is highly covalent, while adjacent layers are held together by ionic forces or van der Waals interactions. These latter forces can frequently be neutralized by relatively modest chemical means, while the bonding between atoms within the layers remains intact and unaffected.

In one embodiment the mesoporous material exhibits an X-ray diffraction pattern, after calcination, with at least one peak at a position greater than about 18 Angstrom Units d-spacing with a relative intensity of 100, and has a benzene adsorption capacity of greater than about 15 grams benzene per 100 grams of the anhydrous material at 50 torr (6.7 kPa) and 25° C. One example of such a mesoporous support material is MCM-41, which has a hexagonal arrangement of uniformly-sized pores and is described in U.S. Pat. No. 5,098,684, the entire contents of which are incorporated herein by reference. Other suitable support materials include MCM-48, which has a cubic symmetry and is described in U.S. Pat. No. 5,198,203, and MCM-50, which has a lamellar structure and is described in U.S. Pat. No. 5,304,363. The entire contents of both of these patents are incorporated herein by reference.

In one embodiment, an additional hydroalkylation catalyst component that may be added or composited with the hydroalkylation catalyst includes an inorganic oxide. The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as silica, alumina, titania, and/or zirconia. As used herein, the numbering scheme for the Periodic Table Groups is as disclosed in Chemical and Engineering News, 63(5), 27 (1985).

In another embodiment, at least a portion of the hydrogenation metal component is supported on the additional hydroalkylation catalyst component separate from but composited with the molecular sieve of the MCM-22 family. The additional hydroalkylation catalyst component includes the inorganic, crystalline, mesoporous support material or inorganic oxide or a combination thereof. In one embodiment, the hydrogenation metal component may be deposited on the additional hydroalkylation catalyst component, conveniently by impregnation, before the additional hydroalkylation catalyst component is composited with the molecular sieve of the MCM-22 family. In another embodiment, the hydrogenation metal component may be deposited on the hydroalkylation catalyst composite by way of impregnation such as anionic impregnation.

Typically, the catalyst composite is produced by co-pelletization, in which a mixture of the molecular sieve and the metal-containing inorganic oxide are formed into pellets at high pressure (generally about 350 to about 350,000 kPa), by co-extrusion, in which a slurry of the molecular sieve and the metal-containing inorganic oxide, optionally together with a separate binder, are forced through a die, or by extrusion, in which a mixture of molecular sieve and inorganic oxide, optionally together with a separate binder, are forced through a die wherein the metal is added to the catalyst composition after extrusion. If necessary, additional hydrogenation metal component can subsequently be deposited on the resultant catalyst composite.

A binder material in addition to the catalyst components described herein may be added or composited with the hydroalkylation catalyst. Suitable binder materials include synthetic or naturally occurring substances as well as inorganic materials such as clay, silica and/or inorganic oxide. The inorganic oxide may a metal oxide and may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction using an MCM-22 family zeolite catalyst is highly selective towards cyclohexylbenzene, the effluent from the hydroalkylation reaction will inevitably contain significant quantities of benzene and certain by-products in addition the desired cyclohexylbenzene. Generally, the major by-products are cyclohexane and dicyclohexylbenzene although, as indicated previously, the addition of the diluents to the hydroalkylation reaction has the advantage of significantly reducing the amount of the dicyclohexylbenzene by-product. In one embodiment, the cyclohexane by-product is recycled back to the hydroalkylation reactor to be utilized as at least one diluent in the hydroalkylation reaction. In this embodiment, the cyclohexane can be cycled up to the directed weight ratio with the benzene fed to the hydroalkylation reactor. The utilization of cyclohexane as the diluent has the advantage of utilizing an unwanted by-product that would normally be purged or dehydrogenated to benzene and recycled back to the hydroalkylation reactor.

A multi-stage distillation process is therefore used to divide the hydroalkylation reaction product into (i) a $C_6$-rich stream comprising cyclohexane and benzene, (ii) a cyclohexylbenzene-rich stream and (iii) a heavies stream rich in dicyclohexylbenzene. Owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluent.

When a stream is described as being "rich" in a specified species, it is meant that the specified species in that stream is enriched relative to other species in the same stream or composition on a weight percentage basis. For illustration purposes only, a cyclohexylbenzene-rich stream will have a cyclohexylbenzene wt % greater than any other species or component in that same stream. A "$C_6$" species generally means any species containing 6 carbon atoms.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The ratio of benzene to cyclohexane recycled back to the hydroalkylation reactor may be managed by this dehydrogenation of at least a portion of the $C_6$-rich stream. In one embodiment, at least a portion of the $C_6$-rich stream bypasses the dehydrogenation step so that at least a portion of the cyclohexane in the hydroalkylation effluent is recycled back to the hydroalkylation reactor.

The dehydrogenation catalyst generally comprises (a) a support; (b) a hydrogenation-dehydrogenation component; (c) an inorganic promoter; and (d) optionally a binder. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa), a weight hourly space velocity of about 0.2 to 50 $hr^{-1}$, and a hydrogen to hydrocarbon feed molar ratio of about 0 to about 20.

Depending on the amount of dicyclohexylbenzene present in the heavies stream (iii), it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, including large pore molecular sieves such as a molecular sieve of the MCM-22 family, zeolite beta, MCM-68 (see U.S. Pat. No. 6,014,018), zeolite Y, zeolite USY, and mordenite. A large pore molecular sieve has an average pore size in excess of 7 Å in some embodiments or from 7 Å to 12 Å in other embodiments. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1. The transalkylation reaction effluent can then be returned to the second distillation tower to recover the additional monocyclohexylbenzene product produced in the transalkylation reaction.

Dealkylation or cracking is also typically effected in a reactor separate from the hydroalkylation reactor, such as a reactive distillation unit, at a temperature of about 150° C. to about 500° C. and a pressure of 15 to 500 psig (200 to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

The cyclohexylbenzene-rich stream (ii) separated from the hydroalkylation reaction product is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 mol % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 2.0 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the following non-limiting Examples.

In the Examples, a catalyst comprising 0.15 wt % Pd/80 wt % MCM-49/20 wt % alumina was used. A mixture of 80% MCM-49, 20% alumina, and deionized (DI) water was extruded to form a catalyst for testing. The catalyst was used in extrudate form wherein the extrudate was cut into particles of L/D (length/diameter) of roughly one. The extrudate was then calcined and then ammonium exchanged with 1 N ammonium nitrate solution, followed by the final air calcination at 538° C. to form h-form extrudate. The resulting extrudate was then treated with anionic PdCl2 in HCl solution (nominally known as H2PdCl4) using an aqueous based incipient wetness impregnation method wherein the H2PdCl2 was diluted in DI water. The treated catalyst was air dried at 121° C. and calcined in air at 360° C. for 2 hours to form the 0.15 wt % of MCM-49 bound with alumina catalyst.

For each experiment, 700 mg of catalyst extrudate particles were mixed with 1 gram of 40 mesh quartz chips, and the mixture was packed into a 0.25 inch (0.64 cm) outer diameter stainless steel reactor. The catalyst was pretreated by heating up to 300° C. and holding at 300° C. for 2 hours under 50 standard cubic centimeters per minute (sccm) of hydrogen gas flow. The reactor temperature was then reduced to desired temperature prior to feed introduction. The feed was delivered using an ISCO pump and was vaporized prior to mixing with hydrogen. The mixture was fed into the reactor in downflow mode. The reaction was run at 145° C. and 165 psig (1240 kPa) total reactor pressure. The effluent from the reactor was analyzed using an offline gas chromatograph (GC) equipped with a flame ionization detector (FID) for analysis. All the hydrocarbons were analyzed and the results were normalized.

EXAMPLE 1

Comparative

A control experiment was performed using 100% benzene as feed. Table 1 shows the results for benzene hydroalkylation to cyclohexylbenzene (CHB) versus time on stream (TOS) at 145° C., 165 psig (1240 kPa) total reactor pressure, and H2/benzene molar ratio of 0.70. The benzene flow rate was adjusted to vary weight hourly space velocity (WHSV) and the benzene conversion.

TABLE 1

| TOS, hrs | 84 | 90 | 96 | 102 | 108 | Average |
|---|---|---|---|---|---|---|
| Feedrate, microliter/min | 47 | 47 | 70 | 70 | 70 | |
| Bz, wt % | 100 | 100 | 100 | 100 | 100 | |
| Decane, wt % | 0 | 0 | 0 | 0 | 0 | |
| WHSV(hr-1) | 3.52 | 3.52 | 5.24 | 5.24 | 5.24 | |
| H2/benzene | 0.70 | 0.70 | 0.70 | 0.70 | 0.70 | |
| CHB, wt % | 16.25 | 15.01 | 12.75 | 12.70 | 12.38 | 13.82 |
| m-DCHB, wt % | 0.97 | 0.87 | 0.51 | 0.51 | 0.48 | 0.67 |
| p-DCHB, wt % | 0.91 | 0.78 | 0.52 | 0.51 | 0.48 | 0.64 |
| benzene conversion, wt % | 21.21 | 18.81 | 15.38 | 15.17 | 14.72 | 17.06 |
| total diCHB, wt % | 1.87 | 1.64 | 1.03 | 1.02 | 0.95 | 1.30 |
| total heavies, wt % | 2.05 | 1.77 | 1.10 | 1.09 | 1.02 | 1.41 |
| diCHB/CHB | 11.54 | 10.95 | 8.04 | 8.02 | 7.71 | 9.25 |
| total heavies/CHB | 12.62 | 11.79 | 8.64 | 8.56 | 8.25 | 9.97 |

From Table 1 it will be seen that, as the benzene conversion was varied between 14 wt % and 21 wt %, the yield of cyclohexylbenzene (CHB) increased from about 12 wt % to about 16 wt %, whereas the total yield of dicyclohexylbenzene (diCHB), also individually measured as meta-dicyclohexylbenzene (m-DCHB) and para-dicyclohexylbenzene (p-DCHB) in Table 1, increased from about 1 wt % to 2 wt %. Note that the yield of diCHB or total heavies is dependent upon the yield of CHB. It is therefore more meaningful to compare the weight ratio of diCHB/CHB or the weight ratio of the total heavies/CHB under similar CHB yield. For the benzene feed without dilution, the average weight ratio of diCHB/CHB was 9.25.

EXAMPLE 2

25 wt % Benzene/75 wt % Decane Feed

The process of Example 1 was repeated but with the benzene feed being diluted with decane. The results are shown in Table 2. Note that similar to the control experiment, CHB yield was kept similar to the control experiment so that the results are comparable. At an average CHB yield of 13.55 wt %, comparable to that of the control experiment at 13.82 wt %, the ratio of diCHB/CHB was measured to be 3.93, which is 58% less than that of the control experiment. The results suggest that the amount of diCHB was significantly reduced as a result of the decane dilution. Similarly, the amount of heavies decreased from an average of 1.41 wt % to 0.72 wt %, a reduction of almost 50%.

TABLE 2

| TOS, hrs | 66 | 72 | 114 | 120 | 126 | Average |
|---|---|---|---|---|---|---|
| Feedrate, microliter/min | 153 | 153 | 153 | 153 | 153 | |
| Bz, wt % | 25 | 25 | 25 | 25 | 25 | |
| Decane, wt % | 75 | 75 | 75 | 75 | 75 | |
| WHSV(hr-1) | 2.50 | 2.50 | 2.50 | 2.50 | 2.50 | |
| H2/benzene | 0.99 | 0.99 | 0.99 | 0.99 | 0.99 | |
| CHB, wt % | 13.01 | 13.06 | 14.58 | 14.07 | 13.03 | 13.55 |
| m-DCHB, wt % | 0.24 | 0.25 | 0.30 | 0.28 | 0.23 | 0.26 |
| p-DCHB, wt % | 0.26 | 0.25 | 0.30 | 0.31 | 0.27 | 0.28 |
| benzene conversion, wt % | 19.02 | 19.42 | 18.19 | 18.25 | 16.92 | 18.36 |
| total diCHB, wt % | 0.49 | 0.49 | 0.61 | 0.58 | 0.50 | 0.53 |
| total heavies, wt % | 0.70 | 0.71 | 0.78 | 0.76 | 0.65 | 0.72 |
| diCHB/CHB, % | 3.77 | 3.78 | 4.15 | 4.15 | 3.82 | 3.93 |
| total heavies/CHB, % | 5.40 | 5.42 | 5.34 | 5.39 | 5.00 | 5.31 |

The results clearly demonstrate that solvents such as decane can significantly reduce the amount of diCHB and heavies in the hydroalkylation.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

Additionally or alternately, the invention can be described by the following embodiments:

1. A process for producing a cycloalkylaromatic compound, the process comprising:
   (a) supplying an aromatic compound, hydrogen and at least one diluent to a hydroalkylation reaction zone, wherein the weight ratio of the diluent to the aromatic compound supplied to the hydroalkylation reaction zone, as measured at the input to the hydroalkylation reaction zone, is in the range from 1:100 to 100:1 and wherein the molar ratio of hydrogen to the aromatic compound supplied to the hydroalkylation reaction zone, as measured at the input to the hydroalkylation reaction zone, is in the range from 1:100 to 100:1; and
   (b) contacting the aromatic compound, hydrogen and the at least one diluent under hydroalkylation conditions with a hydroalkylation catalyst in the hydroalkylation reaction zone to produce an effluent comprising a cycloalkylaromatic compound.
2. The process of embodiment 1, wherein the weight ratio of the diluent to the aromatic compound supplied to the hydroalkylation reaction zone is in the range from 1:10 to 100:1.
3. The process of embodiment 1, wherein the weight ratio of the diluent to the aromatic compound supplied to the hydroalkylation reaction zone is from 1:10 to 4:1.
4. The process of embodiment 1, wherein the hydroalkylation catalyst comprises at least one hydrogenation metal component.
5. The process of embodiment 4, wherein the at least one hydrogenation metal component is selected from Groups 8 to 10 of the Periodic Table of the Elements.
6. The process of embodiment 4, wherein the at least one hydrogenation metal component is selected from palladium, ruthenium, nickel, zinc, tin, and cobalt.
7. The process of embodiment 4, wherein the hydroalkylation catalyst also comprises at least one molecular sieve.
8. The process of embodiment 7, wherein the at least one molecular sieve comprises an MCM-22 family molecular sieve.
9. The process of embodiment 1, wherein the catalyst further comprises an inorganic, crystalline, mesoporous material.
10. The process of embodiment 9, wherein the mesoporous material exhibits an X-ray diffraction pattern, after calcination, with at least one peak at a position greater than about 18 Angstrom Units d-spacing with a relative intensity of 100, and has a benzene adsorption capacity of greater than about 15 grams benzene per 100 grams of the anhydrous support material at 50 torr (6.7 kPa) and 25° C.
11. The process of embodiment 9, wherein the mesoporous material is MCM-41.
12. The process of embodiment 1, wherein the diluent is at least one compound selected from a straight chain paraffinic hydrocarbon, a branched chain paraffinic hydrocarbon, and a cyclic paraffinic hydrocarbon.
13. The process of embodiment 1, wherein the aromatic compound is benzene and the cycloalkylaromatic compound is cyclohexylbenzene and wherein the effluent further comprises cyclohexane.
14. The process of embodiment 13, wherein the process further comprises recycling at least a portion of the cyclohexane to the contacting step (a) wherein the cyclohexane is utilized as the at least one diluent.
15. The process of embodiment 1, wherein the addition of the diluent reduces the weight ratio of dicyclohexylbenzene to cyclohexylbenzene in the effluent.
16. The process of embodiment 1, wherein the addition of the diluent reduces the weight ratio of dicyclohexylbenzene to cyclohexylbenzene contained in the effluent by ten percent as compared to the weight ratio of dicyclohexylbenzene to cyclohexylbenzene in a hydroalkylation process under the same hydroalkylation conditions wherein substantially no diluent is added to the hydroalkylation reaction zone.
17. The process of embodiment 1, wherein the addition of the diluent reduces the weight ratio of dicyclohexylbenzene to cyclohexylbenzene contained in the effluent by twenty five percent as compared to the weight ratio of dicyclohexylbenzene to cyclohexylbenzene in a hydroalkylation process under the same hydroalkylation conditions wherein substantially no diluent is added to the hydroalkylation reaction zone.
18. The process of embodiment 1, wherein the addition of the diluent reduces the weight ratio of dicyclohexylbenzene to cyclohexylbenzene contained in the effluent by fifty percent as compared to the weight ratio of dicyclohexylbenzene to cyclohexylbenzene in a hydroalkylation process under the same hydroalkylation conditions wherein substantially no diluent is added to the hydroalkylation reaction zone.
19. The process of embodiment 1, wherein the addition of the diluent reduces the amount of dicyclohexylbenzene produced in the effluent hydroalkylation reaction zone.
20. The process of embodiment 1, wherein the addition of the diluent reduces the amount of heavies produced in the hydroalkylation reaction zone.
21. The process of embodiment 13, and further comprising:
   (c) separating at least a portion of the effluent into at least a cyclohexylbenzene-rich stream and a $C_6$ product stream comprising cyclohexane and benzene; and
   (d) recycling at least a portion of the $C_6$ product stream to the contacting step (a) wherein the cyclohexane in the $C_6$ product stream portion is utilized as the at least one diluent.
22. The process of embodiment 21, and further comprising:

(e) supplying a further portion of the $C_6$ product stream to a dehydrogenation reaction zone;

(f) contacting the further portion of the $C_6$ product stream with a dehydrogenation catalyst in the second dehydrogenation reaction zone under dehydrogenation conditions to convert at least part of the cyclohexane in the further $C_6$ product stream portion into benzene; and (g) recycling the benzene from the contacting step (f) to the contacting step (a).

23. The process of embodiment 22, and further comprising:

(h) oxidizing at least part of the cyclohexylbenzene-rich stream to produce cyclohexylbenzene hydroperoxide; and (i) converting at least part of the cyclohexylbenzene hydroperoxide from the oxidizing step (h) to produce phenol and cyclohexanone.

24. The process of claim 23, wherein at least a portion of the phenol is converted to at least one of a phenolic resin, bisphenol A, ε-caprolactam, an adipic acid or a plasticizer.

25. The process of claim 23, wherein at least a portion of the cyclohexanone is converted into at least one of adipic acid, a cyclohexanone resin, a cyclohexanone oxime, caprolactam or nylon.

26. A process for producing cyclohexylbenzene, the process comprising:

(a) supplying benzene, hydrogen and at least one diluent to a hydroalkylation reaction zone, wherein the weight ratio of the diluent to the benzene supplied to the hydroalkylation reaction zone is in the range from 1:100 to 100:1 and wherein the diluent supplied to the hydroalkylation reaction zone derives from a source separate and apart from the benzene;

(b) contacting the benzene, the hydrogen and the at least one diluent under hydroalkylation conditions with a hydroalkylation catalyst in the hydroalkylation reaction zone to produce an effluent comprising cyclohexylbenzene;

(c) separating at least a portion of the effluent into at least a cyclohexylbenzene-rich stream and a $C_6$ product stream comprising cyclohexane and benzene; and (d) recycling at least a portion of the $C_6$ product stream to the contacting step (a) wherein the cyclohexane in the $C_6$ product stream portion is utilized as the at least one diluent.

27. A process for producing cyclohexylbenzene, the process comprising:

(a) supplying benzene, hydrogen and at least one diluent to a hydroalkylation reaction zone, wherein the weight ratio of the diluent to the benzene supplied to the hydroalkylation reaction zone is in the range from 1:10 to 100:1;

(b) contacting the benzene, hydrogen and the at least one diluent under hydroalkylation conditions with a hydroalkylation catalyst in the hydroalkylation reaction zone to produce an effluent comprising cyclohexylbenzene;

(c) separating at least a portion of the effluent into at least a cyclohexylbenzene-rich stream and a $C_6$ product stream comprising cyclohexane and benzene; and (d) recycling at least a portion of the $C_6$ product stream to the contacting step (a) wherein the cyclohexane in the $C_6$ product stream portion is utilized as the at least one diluent;

wherein the addition of the diluent reduces the weight ratio of dicyclohexylbenzene to cyclohexylbenzene in the effluent.

The invention claimed is:

1. A process for producing a cycloalkylaromatic compound, the process comprising:

(a) supplying an aromatic compound, hydrogen and at least one diluent to a hydroalkylation reaction zone, wherein the weight ratio of the diluent to the aromatic compound supplied to the hydroalkylation reaction zone, as measured at the input to the hydroalkylation reaction zone, is in the range from 1:100 to 100:1 and wherein the molar ratio of hydrogen to the aromatic compound supplied to the hydroalkylation reaction zone, as measured at the input to the hydroalkylation reaction zone, is in the range from 1:100 to 100:1; and (b) contacting the aromatic compound, hydrogen and the at least one diluent under hydroalkylation conditions with a hydroalkylation catalyst in the hydroalkylation reaction zone to produce an effluent comprising a cycloalkylaromatic compound, wherein the hydroalkylation catalyst comprises an MCM-22 family molecular sieve, and the addition of the diluent reduces the weight ratio of dicyclohexylbenzene to cyclohexylbenzene in the effluent.

2. The process of claim 1, wherein the weight ratio of the diluent to the aromatic compound supplied to the hydroalkylation reaction zone is in the range from 1:10 to 100:1.

3. The process of claim 1, wherein the weight ratio of the diluent to the aromatic compound supplied to the hydroalkylation reaction zone is from 1:10 to 4:1.

4. The process of claim 1, wherein the hydroalkylation catalyst comprises at least one hydrogenation metal component.

5. The process of claim 4, wherein the at least one hydrogenation metal component is selected from Groups 8 to 10 of the Periodic Table of the Elements.

6. The process of claim 4, wherein the at least one hydrogenation metal component is selected from palladium, ruthenium, nickel, zinc, tin, and cobalt.

7. The process of claim 1, wherein the catalyst further comprises an inorganic, crystalline, mesoporous material.

8. The process of claim 7, wherein the mesoporous material exhibits an X-ray diffraction pattern, after calcination, with at least one peak at a position greater than about 18 Angstrom Units d-spacing with a relative intensity of 100, and has a benzene adsorption capacity of greater than about 15 grams benzene per 100 grams of the anhydrous support material at 50 torr (6.7 kPa) and 25° C.

9. The process of claim 7, wherein the mesoporous material is MCM-41.

10. The process of claim 1, wherein the diluent is at least one compound selected from a straight chain paraffinic hydrocarbon, a branched chain paraffinic hydrocarbon, and a cyclic paraffinic hydrocarbon.

11. The process of claim 1, wherein the aromatic compound is benzene and the cycloalkylaromatic compound is cyclohexylbenzene and wherein the effluent further comprises cyclohexane.

12. The process of claim 11, wherein the process further comprises recycling at least a portion of the cyclohexane to the contacting step (a) wherein the cyclohexane is utilized as the at least one diluent.

13. The process of claim 1, wherein the addition of the diluent reduces the weight ratio of dicyclohexylbenzene to cyclohexylbenzene contained in the effluent by ten percent as compared to the weight ratio of dicyclohexylbenzene to cyclohexylbenzene in a hydroalkylation process under the same hydroalkylation conditions wherein substantially no diluent is added to the hydroalkylation reaction zone.

14. The process of claim 1, wherein the addition of the diluent reduces the weight ratio of dicyclohexylbenzene to cyclohexylbenzene contained in the effluent by twenty five percent as compared to the weight ratio of dicyclohexylbenzene to cyclohexylbenzene in a hydroalkylation process under the same hydroalkylation conditions wherein substantially no diluent is added to the hydroalkylation reaction zone.

15. The process of claim 1, wherein the addition of the diluent reduces the weight ratio of dicyclohexylbenzene to cyclohexylbenzene contained in the effluent by fifty percent as compared to the weight ratio of dicyclohexylbenzene to cyclohexylbenzene in a hydroalkylation process under the same hydroalkylation conditions wherein substantially no diluent is added to the hydroalkylation reaction zone.

16. The process of claim 1, wherein the addition of the diluent reduces the amount of dicyclohexylbenzene produced in the effluent hydroalkylation reaction zone.

17. The process of claim 1, wherein the addition of the diluent reduces the amount of heavies produced in the hydroalkylation reaction zone.

18. The process of claim 11, and further comprising:
(c) separating at least a portion of the effluent into at least a cyclohexylbenzene-rich stream and a $C_6$ product stream comprising cyclohexane and benzene; and
(d) recycling at least a portion of the $C_6$ product stream to the contacting step (a) wherein the cyclohexane in the $C_6$ product stream portion is utilized as the at least one diluent.

19. The process of claim 18, and further comprising:
(e) supplying a further portion of the $C_6$ product stream to a dehydrogenation reaction zone;
(f) contacting the further portion of the $C_6$ product stream with a dehydrogenation catalyst in the second dehydrogenation reaction zone under dehydrogenation conditions to convert at least part of the cyclohexane in the further $C_6$ product stream portion into benzene; and
(g) recycling the benzene from the contacting step (f) to the contacting step (a).

20. The process of claim 19, and further comprising:
(h) oxidizing at least part of the cyclohexylbenzene-rich stream to produce cyclohexylbenzene hydroperoxide; and
(i) converting at least part of the cyclohexylbenzene hydroperoxide from the oxidizing step (h) to produce phenol and cyclohexanone.

21. The process of claim 20, wherein at least a portion of the phenol is converted to at least one of a phenolic resin, bisphenol A, ε-caprolactam, an adipic acid or a plasticizer.

22. The process of claim 20, wherein at least a portion of the cyclohexanone is converted into at least one of adipic acid, a cyclohexanone resin, a cyclohexanone oxime, caprolactam or nylon.

* * * * *